United States Patent [19]

Isotalo

[11] Patent Number: 4,960,002
[45] Date of Patent: Oct. 2, 1990

[54] SAMPLER FOR LIQUID SUBSTANCES

[76] Inventor: Ilkka Isotalo, Rossinkatu 2 E 17, SF-20380 Turku, Finland

[21] Appl. No.: 382,695

[22] PCT Filed: Feb. 12, 1988

[86] PCT No.: PCT/FI88/00022
§ 371 Date: Aug. 8, 1989
§ 102(e) Date: Aug. 8, 1989

[87] PCT Pub. No.: WO88/06285
PCT Pub. Date: Aug. 25, 1988

[30] Foreign Application Priority Data
Feb. 13, 1987 [FI] Finland ............... 870608

[51] Int. Cl.⁵ ............................... G01N 1/12
[52] U.S. Cl. .................................. 73/864.67
[58] Field of Search ........... 73/864.67, 864.66, 864.65, 73/864.63

[56] References Cited

U.S. PATENT DOCUMENTS

| 1,857,537 | 5/1932 | Frank et al. ............... 73/864.63 |
| 1,887,859 | 11/1932 | Pearce ................... 73/864.65 X |
| 3,459,048 | 8/1969 | Bicknell .................... 73/864.63 |
| 3,489,012 | 1/1970 | Niskin . |
| 3,714,830 | 2/1973 | Keir . |
| 3,815,422 | 6/1974 | Niskin . |
| 3,845,303 | 10/1974 | Richards et al. ............. 250/303 |
| 4,593,570 | 6/1986 | Niskin ...................... 73/864.67 |
| 4,754,654 | 7/1988 | Johnson et al. ........... 73/864.67 X |

FOREIGN PATENT DOCUMENTS

| 2803593 | 8/1979 | Fed. Rep. of Germany . |
| 1598927 | 8/1970 | France . |
| 2158626 | 6/1973 | France . |
| 562747 | 6/1977 | U.S.S.R. ................. 73/864.66 |
| 744267 | 6/1980 | U.S.S.R. ................. 73/864.66 |
| 800783 | 2/1981 | U.S.S.R. ................. 73/864.63 |
| 851167 | 7/1981 | U.S.S.R. ................. 73/864.63 |

Primary Examiner—Tom Noland
Attorney, Agent, or Firm—St. Onge Steward Johnston & Reens

[57] ABSTRACT

Sampler (1) for liquid substances, especially a water sampler, comprising a body (2), a sampling container (3) fitted with a sealable bottom (6) and cover (7), as well as a closure for closing the sampling container (3) of sampler (1) to be immersed in liquid upon a lowering cable (8), the closing being effected at a desired depth by a weight (13) to be dropped along the cable. The sampling container (3) is mounted for axial movement on body (2) external of the container. Body (2) is provided with a release mechanism (4) from which container (3) can be suspended in an upper position relative to body (2) upon a laterally hinged cover (7) which is in an open position. Hook (10) and peg (11) are provided for locking the laterally hinged bottom (6) of the upper positioned container (3) in an open position. The container (3) released by release mechanism (4) is adapted to slide under gravity along body (2) down to a lower position, the cover (7) being adapted to close by the action of gravity and bottom (6) and/or the lower section of body (2) is provided with a sliding surface (27) which, as container (3) is moving downwards under gravity, forces bottom (6) to close and to remain closed.

10 Claims, 3 Drawing Sheets

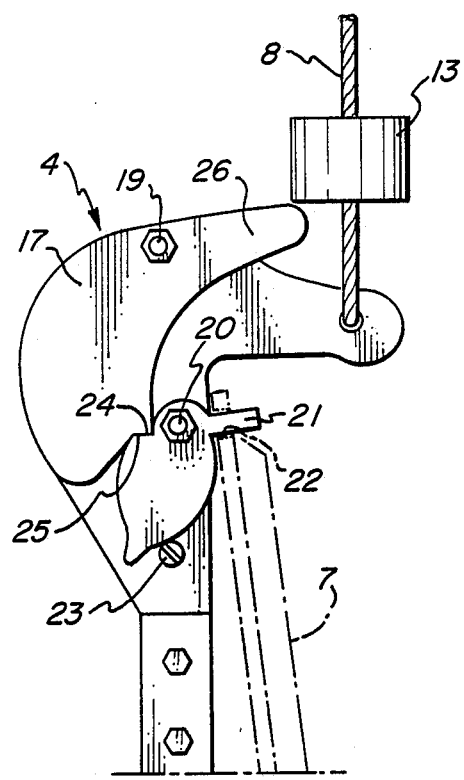
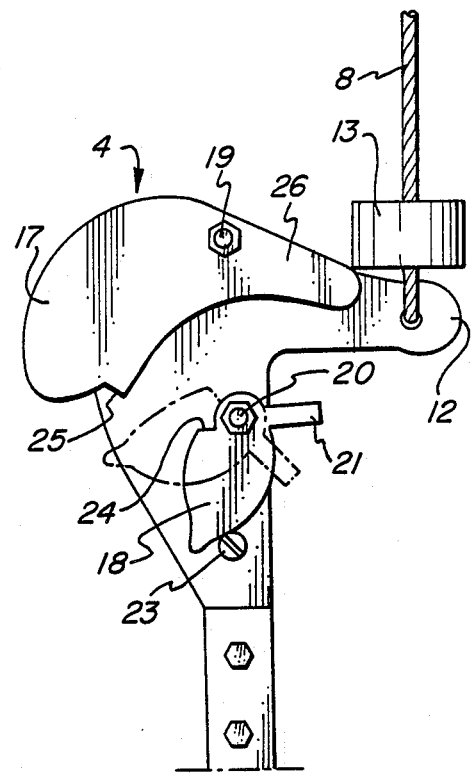
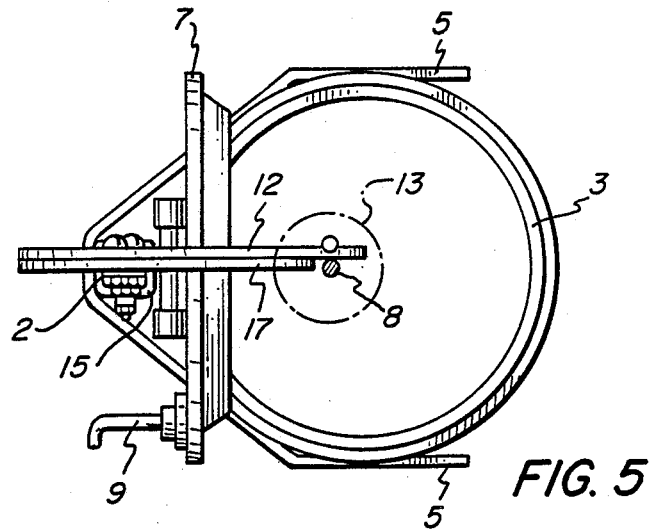

SAMPLER FOR LIQUID SUBSTANCES

BACKGROUND OF THE INVENTION

The present invention relates to a sampler for liquid substances, especially a water sampler, comprising a body, a sampling container fitted with a sealable bottom and cover, as well as means for closing the sampling container of a sampler to be immersed in liquid upon a lowering cable at a desired depth by means of a weight dropped along said cable.

This type of samplers are particularly useful in limnological studies for picking up water samples from desired depths. The device is lowered down to s sampling depth in an open condition, it is closed by means of a weight dropped along a fastening cable and lifted up to the surface.

Various samplers have been used a long time for studying the condition and quality of waterways. Previously known is a so-called "Ruttner" sampler, comprising a cylindrical container whose bottom and cover, while maintaining their orientation, can be brought into an opened position from which a mechanism extending through the container retracts the sampler into a closed position whenever desired. Prior known are also models in which the covers at a lowering stage are set to be parallel to the vertical walls of a container portion, whereby the covers do not interfere with the changing of water in the container cylinder. In these models, at least the bottom cover is closed by means of a spring or lever system released with a throw weight. Prior known are also devices in which a cylinder is closed at a sampling depth by means of rubber plugs pulled into position by a rubber band stretched through the cylinder.

The following drawbacks can be mentioned in connection with the prior art samplers. Due to its poor flowthrough, the "Ruttner" type carries water from above down to the release depth. Since that model, the same as other models, has structural elements in its container cylinder, the equipment is hard to keep clean and objectionable matter may be released into a sample.

In models, wherein the flaps are hinged to open sideways, a drawback in intensive use and corrosion-inducing circumstances is that the spring systems of said covers are easily damaged and this, among other things, tends to cause leaks through the bottom cover. The samplers are generally heavy and daily work may take even several hours subjecting a worker to extra stress. In normal operation, the samplers must be held manually during drainage and e.g. the discharge cock is ordinarily at the bottom and thus difficult to handle. Aside from a few models used by marine researchers, the samplers cannot be fastened in series to one and the same cable in order to essentially reduce the working hours and often e.g. save expensive vessel-operating time.

The release mechanisms of the prior art models generally employ springs whose strength changes over extended use, which is why the device may release itself at a wrong depth or a throw weight shall not be sufficient to release it at all.

Structurally many samplers are complicated, include a plurality of minor components and modern rapid working techniques cannot be applied to their manufacture.

An object of the invention is to eliminate these drawbacks encountered in the above prior art samplers.

SUMMARY OF THE INVENTION

According to the invention, this objective is resolved in a manner that a sampling container is mounted for axial movement on a body external of the container, that the body is provided with a release mechanism for suspending the container therefrom in an upper position relative to the body upon an opened, laterally hinged cover, that means are provided for locking in an open position the laterally hinged bottom of the container in said upper position, and that the container released by a release mechanism is adapted to slide under gravity down the body to a lower position, the cover being adapted to be closed by the action of gravity and the bottom and/or the lower section of said body being provided with means which, as the container is moving downwards under gravity, force the bottom to close and to remain closed.

The release mechanism preferably comprises two flat-shaped elements, a trigger element and a rocker element, each of said elements being rotatably journalled with respect to its own shaft which is fixed relative to the sampler body, the rocker element is provided with a bracket for suspending the container cover, the rocker element is weighted so as to rotate in its unhindered condition relative to the body against a fixed limiter to a basic position, wherein its bracket is substantially horizontal, and the rocker element is provided with an abutment surface against which the matching abutment surface of said trigger element is set as a result of the weighting of said trigger element, said abutment surfaces being relatively arranged so that a downward loading of the bracket of said rocker element produces through the intermediary of said abutment surfaces a force applied to the trigger element and directed roughly towards the shaft of said trigger element, and said trigger element is provided with a bracket whose end is subjected to a force that leads to the inclination of the trigger element and, as a result, to the release of the rocker element.

In one preferred embodiment of the invention, the support stands extending from the vertical body portion are positioned outside the imaginary extension of the envelope surface of a container.

Thus, the means provided at the bottom and/or the lower portion of the body preferably comprise sliding surfaces in the support stands of said body and preferably two laterally extending brackets, fitted to the bottom of a container and adapted for cooperation.

Through a device of the invention, water changes freely at the lowering stage. With the exception of a thermometer fitted therein if so desired, the water chamber of a device does not contain any extra contaminating components either. The device is light-weight and its bottom cover is watertight.

The device has an advantageous volume/weight ratio. The device is ergonomically preferred since, immediately after its lifting, it can be left to stand on its stable base and to effect bottling of the samples without manually holding the deive. By lifting the top cover it is also possible to visually inspect the sample and to determine its odour quite easily. A simple connection of the hose to a socket prevents the hose end from being smeared by sludge near the bottom and also facilitates handling of the hose. Setting up the device is easy since the release mechanism is always returned by gravity to its basic position without any complicated and troublesome corrosion-sensitive components, such as springs.

A plurality of samplers can be connected in series to the same cable.

The release mechanism guarantees that no release occurs at the lowering stage and that a force required for the release always remains constant.

The device can be manufactured from a standard material and several manufacturing steps can be effected by applying high-speed techniques, e.g. plasma cutting.

A sampler of the invention can also be used for special purposes since the diameter and length of a container can be freely selected. For example in view of plankton studies, a sampler of the invention offers an excellent solution by virtue of its opening characteristics and size.

BRIEF DESCRIPTION OF THE DRAWING

The invention will now be described in more detail with reference made to the accompanying drawings.

FIG. 3 is a side view of the release mechanism in a sampler of FIG. 1 just prior to the release instant.

FIG. 4 is a side view according to FIG. 3 after the release instant.

FIG. 5 is a plan view of a sampler set ready for sampling.

DETAILED DESCRIPTION

Figure 1:
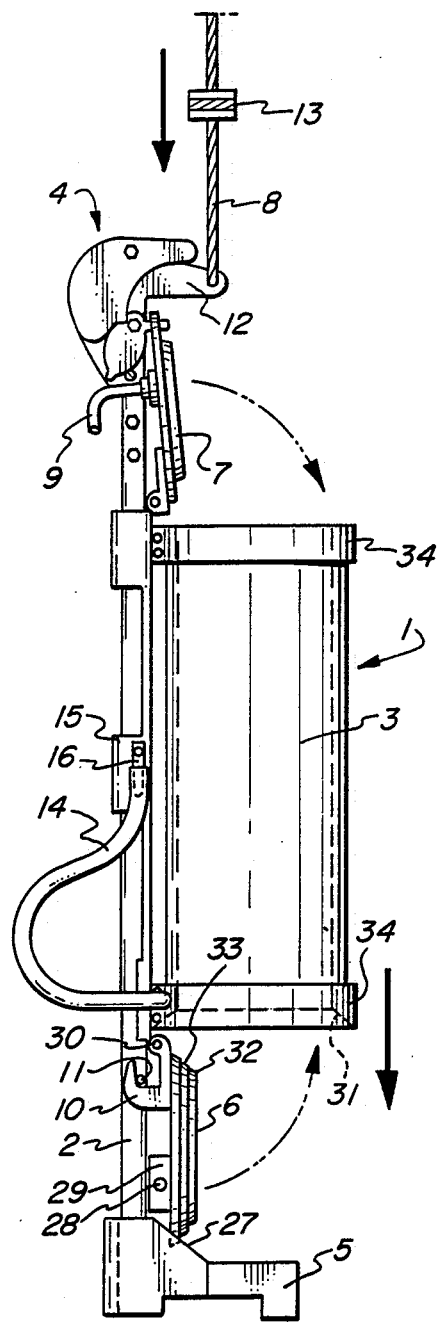
FIG. 1 shows a sampler of the invention in side view, wherein a sampling container is set in its upper position for sampling.

The main applications of a sampler designated generally by reference numeral 1 in FIG. 1 are limnological studies for picking up samples from desired depths.

A sampler 1 comprises a body 2, a sampling container 3 movable therealong, as well as a release mechanism 4. The sampling container 3 is provided with a laterally hinged bottom 6 and a likewise laterally hinged cover 7. Said body 2 of sampler 1 is further provided with support stands 5 on which the sampler can be lowered for storage or draining of the sampling container.

In the position shown in FIG. 1, said sampler 1 is set up ready for immersing the sampler in water by means of a lowering cable 8. In this position, a container 3 is lifted to its upper position relative to body 2, said container 3 hanging upon an opened-up cover 7 from release mechanism 4. As container 3 is lifted to its upper position by means of a finger grip 9 in cover 7, a hook 10 secured to the outer surface of bottom 6 catches a peg 11 protruding alongside the vertical section of body 2 for so locking said bottom 6 in an open position. Said peg 11 can of course be replaced by a hole (not shown) made in body 2, said hook 10 engaging in such a hole as container 3 is being lifted to its upper position.

Figure 2:
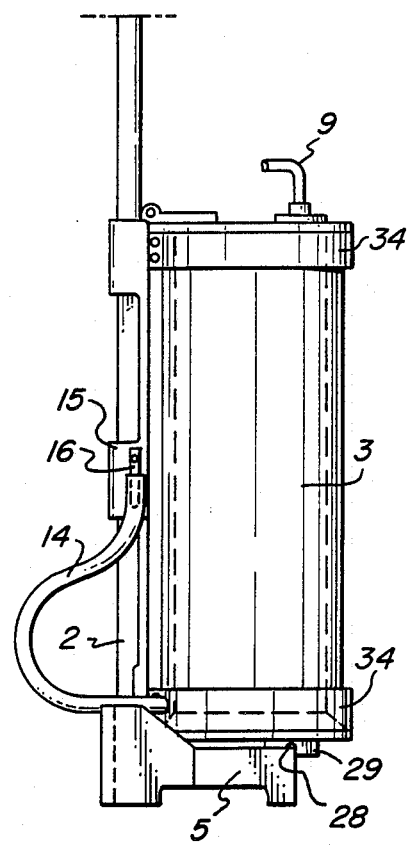
FIG. 2 is a partial view of the sampler shown in FIG. 1 with the exception that a sampling container is in its lower position with the bottom and cover closed.

Lowering cable 8 is fastened by any suitable means to a bracket 12 at the top of body 2 in such a manner that a sampler 1 carried by lowering cable 8 is substantially vertical. A sampler 1 set in an open position as discussed above is lowered by means of lowering cable 8 to a desired depth, whereafter along said lowering cable 8 is lowered a weight 13, comprising preferably e.g. a cylindrical weight element with a hole drilled in the middle for lowering cable 8. As weight 13 meets release mechanism 4, cover 7 is released and container 3 drops by the action of gravity down relative to body member 2, whereby both cover 7 and bottom 6 are closed at the same time (FIG. 2). Thereafter, sampler 1 is lifted up or hoisted upon cable 8 and lowered upon its support stands 5 on a suitable base for draining a sampling container. For recovering a sample, said sampling container 3 is provided with a draining hose 14 connected with the lower container section, a sampling container support member 15 being provided with a socket or chuck 16 for sealing and fastening the free end of such hose. Said socket 16 comprises e.g. a plastic peg upon which the end of hose 14 is pushed.

Reference is made now particularly to FIGS. 3 and 4 which show a release mechanism in a larger scale. A release mechanism 4, which is based only on gravity, comprises two flat-shaped elements, a trigger element 17 and a rocker element 18. Trigger element 17 is rotatably journalled relative to a fixed shaft 19 extending from body 2 of sampler 1. Accordingly, rocker element 18 is rotatably journalled relative to another shaft 20, which is fixed with respect to bracket 12.

The rocker element 18 of said release mechanism 4 is provided with a lug or bracket 21 for suspending the cover 7 of sampling container 3, said cover 7 being provided e.g. with a suitable aperture 22.

The rocker element 18 is weighted in such a manner that in free condition it rotates relative to body 2 against a fixed limiter 23 to a basic position, wherein its bracket 21 is substantially horizontal. Said limiter 23 can be e.g. the head of a screw threaded in body 2.

The rocker element 18 is provided with an abutment surface 24 against which is set a matching abutment surface 25 of trigger element 17 as a result of the weighting of trigger element 17. Abutment surfaces 17, 18 are relatively arranged in a manner that a downward loading of bracket 21 of rocker element 18 produces through the intermediary of abutment surfaces 17, 18 a force applied to trigger element 17 and directed roughly towards shaft 19 of trigger element 17. The trigger element 17 is provided with a bracket 26 whose end is subjected to a force exerted by weight 13 and resulting in the swinging of trigger element 17 around shaft 19 and as a consequence the release of rocker element 18.

In FIG. 3 a release mechanism 4 is shown at the very instant when weight 13 is about to strike bracket 26 of trigger element 17.

In FIG. 4 said weight 13 has depressed bracket 26 of trigger element 17 down and thus released rocker element 18 allowing said rocker element 18, in turn, to swing under the load of cover 7 to a dotted-and-dashed position in which cover 7 has released itself from lug 21 of rocker element 18. After the release, rocker element 18 has returned to its basic position against limiter 23.

The vertical section of body 2 is made of shaped profile, preferably a rectangular tube. Container 3 is fastened to a support member 15, surrounding non-rotatably the shaped profile and preferably made of profiled tube. Said support member 15 extends preferably over nearly the entire height of container 3 and is made partially open to reduce freezing problems.

The support stands 5 extending from the lower portion of body 2 are positioned beyond the imaginary extension of the envelope surface of container 3, as shown particularly in FIG. 5. Support stands 5 are preferably made of sheet metal by cutting and bending and joined with the vertical section of body 2 e.g. by welding.

When release mechanism 4 releases cover 7, container 3 can slide under gravity along body 2 to its lower position. Thus, cover 7 closes only by the action of gravity. On the other hand, bottom 6 and/or the lower portion of body 2 is provided with means which, as container 3 is moving down by the action of gravity, force bottom 6 to close and to remain closed. Such means preferably comprise sliding surfaces 27 in support stands 5 and laterally extending projections in the bottom 6 of container 3, said projections and sliding surfaces being adapted to cooperate with each other. In the present embodiment, said projections are provided by a continuous rod 28, which through the intermediary of a bracing plate 29 is fastened to the outer surface of cover 6. Rod 28 is located relative to bottom 6 in a manner that said rod 28, bearing against support stands 5, together with the linked axle 30 of cover 6 accomplishes a uniform compression of cover 6 against the lower edges of container 3. The lower edge of container 3 is preferably provided with a conical surface 31, against which compresses a matching conical surface 32 in cover 6 together with its sealing 33.

As shown in FIGS. 1 and 5, water is able to change unhindered at the lowering stage of sampler 1. The container 3 of sampler 1 is preferably made of a plexiglass straight circular cylinder, whose upper and lower edges are, if necessary, provided with metallic reinforcement rings 34. Thus, all elements required for supporting and closing a container are positioned outside the container, so the container does not contain any contaminating extra components.

Sampler 1 is entirely made of standard components of plastic or metal. Especially for picking up heavy metal samples, said sampler 1 can also be made entirely of plastics or, alternatively, plastic-coated metal components can be used.

Figure 6:
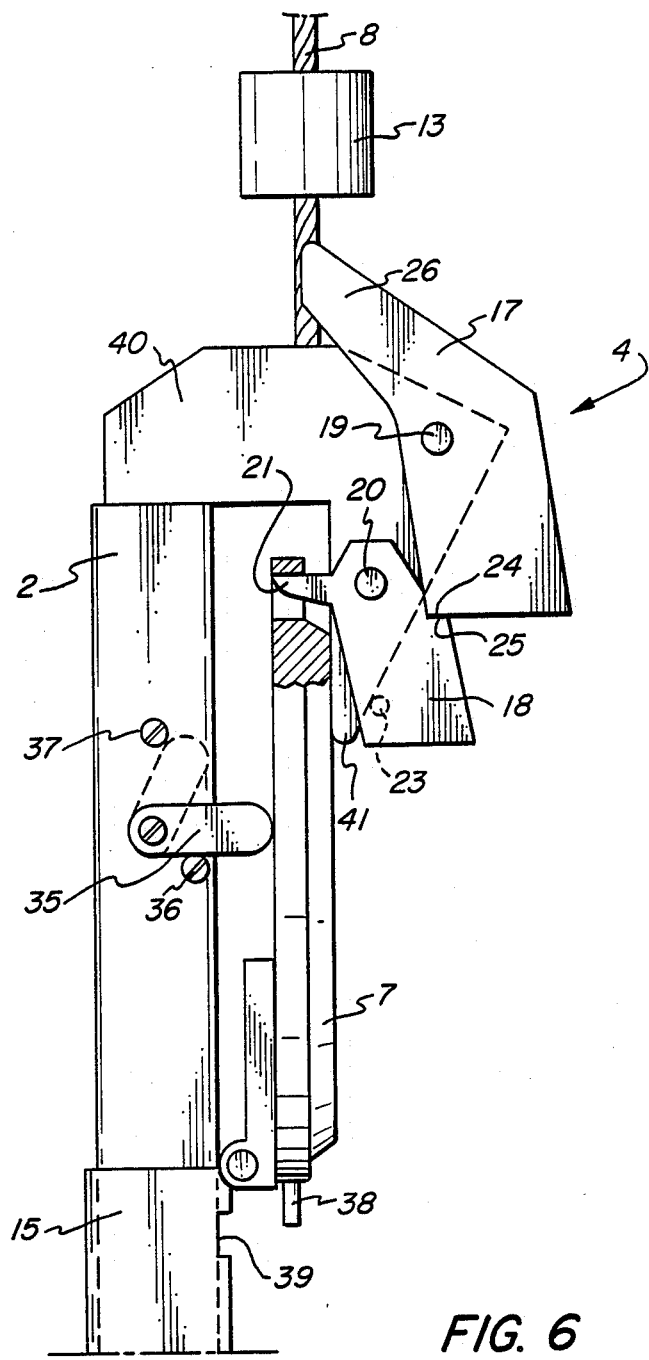
FIG. 6 is a side view of a sampler according to another embodiment of the invention, wherein a sampling container is set to its upper position for sampling.

FIG. 6 illustrates the upper section of a sampler according to another embodiment of the invention, the components corresponding to those in the first embodiment being designated with the same reference numerals.

In a solution shown in FIG. 6, a release mechanism 4 is turned over to the other side compared to the solution of the first embodiment. Body 2 is provided with a freely rotatably journalled safety member 35, comprising a flat-shaped element journalled at one end. The safety member 35 only moves between a horizontal position shown by solid line and an upper position shown by dashed lines. The end positions of safety member 35 are limited by means of pegs or screws 36, 37 secured to body 2.

As cover 7 is lifted up, said safety member 35 swings out of the way but is allowed to drop back to the horizontal position after the cover is pushed into bracket 21 of rocker element 18. In this position, the safety member 35 locks cover 7 in a position it cannot fall off accidentally. At the time of release, as bracket 21 moves down, said cover 7 has space to move down.

A downward-directed extension 41 in the body member 40 of release mechanism 4 is adapted to make sure that the sampler bottom 6 has time to close before cover 7.

In FIG. 6, said cover 7 is provided with a projection 38 and for this projection the support member 15 is provided with a hole 39 and the body portion 2 with another hole (not shown). As the container travels to its lower position, hole 39 will be aligned with said hole in body portion 2, said cover 7 closing and projection 38 setting in said hole. Thus, projection 38 prevents the movement of a closed sampler relative to body 2. This is necessary in order to make sure that the sampler bottom 6 cannot accidentally open. Such a situation is possible e.g. when a boat rolls down from the crest of a wave or lowering cable 8 slips off the hands during lifting.

The invention has been explained above only by refering to a case in which one sampler is carried by a cable. However, it is obvious that an assembly as described above readily makes it possible to connect a plurality of samplers in series as well. On the other hand, a sampler can also mounted rigidly on a suitable rod, whereby the operator will be able to locate the sampler in a proper position when picking up samples from shallow water. The operation of a release mechanism can then be readily facilitated e.g. by using a traction cable.

I claim:

1. A sampler (1) for liquid substances, comprising a body (2), a sampling container (3) fitted with a sealable bottom (6) and cover (7), as well as means for closing said sampling container (3) of sampler (1) to be immersed in liquid upon a lowering cable (8) at a desired depth by means of a weight (13) dropped along said cable, characterized in that said sampling container (3) is mounted for axial movement on a body (2) external of the container, that said body (2) is provided with a release mechanism (4) for suspending container (3) therefrom in an upper position relative to body (2) upon an open-swung, laterally hinged cover (7), that means are provided for locking in an open position said laterally hinged bottom (6) of container (3) in said upper position, and that said container (3) released by release mechanism (4) is adapted to slide under gravity down along body (2) to a lower position, said cover (7) being adapted to be closed by the action of gravity and bottom (6) and the lower section of body (2) being provided with means which, as container (3) is moving downwards under gravity, force bottom (6) to close and to remain closed.

2. A sampler as set forth in claim 1, characterized in that said release mechanism (4) comprises two flat-shaped elements, a trigger element (17) and a rocker element (18), each of said elements being rotatably journalled with respect to its own shaft (19, 20) which is fixed relative to body (2) of sampler (1), that said rocker element (18) is provided with a bracket (21) for suspending cover (7) of container (3), said rocker element (18) is weighted so as to rotate in its unhindered condition relative to body (2) against a fixed limiter (23) to a basic position, wherein its bracket (21) is substantially horizontal, and said rocker element (18) is provided with an abutment surface (24) against which a matching abutment surface (25) in trigger element (17) is set as a result of the weighting of trigger element (17), said abutment surfaces (24, 25) being relatively arranged so that a downward loading of bracket (21) of rocker element (18) produces through the intermediary of abutment surfaces (24, 25) a force applied to trigger element (17) and directed roughly towards shaft (19) of trigger element (17), and that said trigger element (17) is provided with a bracket (26) whose end is subjected to a force that leads to the inclination of trigger element (17) and, as a result, the release of rocker element (18).

3. A sampler as set forth in claim 2, characterized in that said body (2) is provided with a rotatably journalled safety member (35), adapted to automatically swing, after cover 7 is suspended upon bracket (21) of rocker element (18), into a position in which it prevents the inclination of cover (7).

4. A sampler as set forth in claim 1, characterized in that said means for locking bottom (6) in an open position while container (3) is in the upper position comprise a hook-shaped member (10) fastened to the lower surface of bottom (6) and adapted to engage a peg (11) extending from the side of body (2).

5. A sampler as set forth in claim 1, characterized in that the vertical section of body (2) is made of a shaped profile, preferably a rectangular tube, said container (3) being fastened to a support member (15), surrounding non-rotatably said shaped profile and preferably made of a profiled tube.

6. A sampler as set forth in claim 5, characterized in that support stands extending from the vertical section of body (2) are located beyond the imaginary extension of the envelope surface of container (3).

7. A sampler as set forth in claim 5, characterized in that said sampling container (3) is fitted with a draining hose (14), the support member (15) of said sampling container (3) being provided with a socket (16) for sealing and fastening the free end of said hose.

8. A sampler as set forth in claim 1, characterized in that said means mounted on bottom (6) of container (3) and the lower portion of body (2) comprise sliding surfaces (27) in the support stands (5) of body (2) and two laterally extending projections (28) in bottom (6) of container (3), said means being adapted to cooperate with each other.

9. A sampler as set forth in claim 8, characterized in that said projections (28) are so located relative to bottom (6) that, together with a hinge point (30), they divide the periphery of bottom (6) into three substantially equal sections.

10. A sampler as set forth in claim 1, characterized in that said cover (7) is provided with a projection (38) which works its way into a hole in body while cover (7) closes in the lower position of sampler (1).

* * * * *